(12) United States Patent
Passerini et al.

(10) Patent No.: US 12,430,762 B2
(45) Date of Patent: Sep. 30, 2025

(54) ROBUST SHAPE DETERMINATION FOR CARDIAC ANATOMY IN MEDICAL IMAGING

(71) Applicant: SIEMENS HEALTHINEERS AG, Forchheim (DE)

(72) Inventors: Tiziano Passerini, Plainsboro, NJ (US); Edmond Astolfi, Paris (FR); Indraneel Borgohain, East Windsor, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 488 days.

(21) Appl. No.: 18/164,656

(22) Filed: Feb. 6, 2023

(65) Prior Publication Data
US 2024/0054636 A1    Feb. 15, 2024

Related U.S. Application Data

(60) Provisional application No. 63/370,794, filed on Aug. 9, 2022.

(51) Int. Cl.
*G06T 7/00* (2017.01)
*A61B 5/055* (2006.01)
*A61B 6/50* (2024.01)

(52) U.S. Cl.
CPC .......... *G06T 7/0012* (2013.01); *A61B 5/055* (2013.01); *A61B 6/503* (2013.01); *G06T 2207/30048* (2013.01)

(58) Field of Classification Search
CPC ......... G06T 7/0012; G06T 2207/30048; G06T 2207/10088; G06T 2207/20084; G06T 7/33; A61B 5/055; A61B 6/503
See application file for complete search history.

(56) References Cited

U.S. PATENT DOCUMENTS 7,822,246 B2 * 10/2010 Senegas .................. G06T 15/04
600/407
2020/0077892 A1 * 3/2020 Tran ........................ G08B 21/02

OTHER PUBLICATIONS

Acero, Jorge Corral, et al. "Understanding and Improving Risk Assessment After Myocardial Infarction Using Automated Left Ventricular Shape Analysis." 15.9 JACC: Cardiovascular Imaging (2022).

(Continued)

*Primary Examiner* — Shefali D Goradia

(57) ABSTRACT

For shape determination of cardiac anatomy with a medical imager, irregularities in motion, poor image quality, and misalignment of imaging planes are counteracted by a process relying on alignment of contours in combination with selection and fitting of a motion model. Contours are extracted from 2D images and aligned for each frame, which is extracted from the sequence of 2D images. The alignment may use a translation for each frame and rotation across frames for improved performance. A motion model is fit to the aligned contours and tested. If insufficient (greater than threshold difference), other motion models are aligned and tested. Motion models may be created on demand for improved performance. If sufficient, the shape of the heart structure is determined from the fit model.

14 Claims, 3 Drawing Sheets

(56) References Cited

OTHER PUBLICATIONS

Xia, Yan, et al. "Automatic 3D+ t Four-Chamber CMR Quantification of the UK Biobank: integrating imaging and non-imaging data priors at scale." Medical Image Analysis (2022): 102498.

Yang, Lin, et al. "Prediction based collaborative trackers (PCT): A robust and accurate approach toward 3D medical object tracking." IEEE transactions on medical imaging 30.11 (2011): 1921-1932.

* cited by examiner

ROBUST SHAPE DETERMINATION FOR CARDIAC ANATOMY IN MEDICAL IMAGING

RELATED APPLICATION

The present patent document claims the benefit of the filing date under 35 U.S.C. § 119(e) of Provisional U.S. Patent Application Ser. No. 63/370,794, filed Aug. 9, 2022, which is hereby incorporated by reference.

BACKGROUND

The present embodiments relate to cardiac imaging. Cardiac magnetic resonance imaging (MRI), for example, is indicated for the analysis of multiple cardiac conditions. Cardiac MRI acquisition is a lengthy process, resulting in two-dimensional (2D) imaging being preferred to three-dimensional (3D) imaging in most clinical applications. 2D imaging provides sparse spatial sampling of the cardiac anatomy, such as along a plurality of planes or views. Additional processing is required to fully reconstruct the 3D appearance of a cardiac structure, such as a heart chamber. Analysis of the 3D shape of heart chambers is important for the assessment of cardiac function and has the potential of enabling risk stratification in large subject populations.

The 3D shape of heart chambers may not be accurately reconstructed from 2D images for various reasons. Misalignment of 2D imaging planes, such as due to patient motion, respiratory motion artifacts, or incorrect slice planning, may result in poor 3D shape determination. Registration algorithms applied as a post-processing step and the use of shape priors to regularize the registration process and improve slice alignment may help. Poor image quality in specific imaging planes and/or temporal frames may result in poor 3D shape determination. The problem of poor image quality is usually solved by detection of failure of the segmentation algorithm on 2D images followed by exclusion from further analysis of the view and/or temporal frame in which failure is detected. Irregular heart motion and/or beat-to-beat variability may result in poor 3D shape determination. The problem of irregular heart motion is solved by manual selection of the heart beat to be used for further analysis.

SUMMARY

Systems, methods, and non-transitory computer readable media with instructions are provided for shape determination of cardiac anatomy with a medical imager. Irregularities in motion, poor image quality, and misalignment of imaging planes are counteracted by a process relying on alignment of contours in combination with selection and fitting of a motion model. Contours are extracted from 2D images and aligned for each frame, which is extracted from the sequence of 2D images. The alignment may use a translation for each frame and rotation across frames for improved performance. A motion model is fit to the aligned contours and tested. If insufficient (greater than threshold difference), other motion models are aligned and tested. Motion models may be created on demand for improved performance. If sufficient, the shape of the heart structure is determined from the fit model.

In a first aspect, a method is provided for shape determination of cardiac anatomy with a medical imager. The medical imager images a heart of a patient. The imaging generates images representing different planes of the heart at different times. At least a first one of the different planes may not be parallel to second and third ones of the different planes. A structure of the heart in the images of the different planes at the different times is contoured. The contouring provides contours of the structure in the different planes at the different times. Anatomical landmarks of the heart are identified from the images. A cardiac phase for each of the different times is determined from the images. The contours of the different planes are aligned for each of the times. A shape from a first motion model is deformed to the contours as aligned with each other based in part on the anatomical landmarks. The deformed shape from the first motion model is compared to the shape from the motion model. The deformed shape is the shape of the structure of the patient when the comparison shows a threshold similarity. The deforming and comparing are performed for at least one additional motion model when the comparison does not show the threshold similarity until the comparison shows the threshold similarity with one of the at least one additional motion models. Information from the first or additional motion model where the comparison shows the threshold similarity and the shape are displayed.

In one embodiment, the imaging includes cardiac magnetic resonance imaging with six or more short axis views and two or more long axis views as the different planes for each of at least four different times. The different times are over a heart cycle.

In another embodiment, the contouring includes generating a sequence of contours of the structure over the different times for each of the different planes. The structure is a heart chamber.

In yet another embodiment, identifying includes identifying a left ventricle apex, mitral valve annulus points, right ventricle insertion points, tricuspid valve points, and pulmonary veins ostia in the images for each of the different times.

As another embodiment, determining the cardiac phase includes determining one of the different times as end diastole and another of the different times as end systole.

According to an embodiment, aligning the contours includes aligning based on orientation and position information from the imaging and modifying by a rigid transform of the contour from the first plane relative to the contours of the second and third planes based on a minimization of error relative to intersections of the contour from the first plane relative to the contours of the second and third planes.

According to another embodiment, aligning includes aligning the contour from the first plane relative to the contours of the second and third planes in translation for each of the different times and in rotation as a single fit for all the different times using the translation for each of the different times.

In one embodiment, deforming includes selecting the first motion model from a library of motion models, aligning meshes of the first motion model with the anatomical landmarks for the different times, and refining the alignment using the contours.

As an embodiment, the additional motion model is created on demand when the comparison to the first motion model does not show the threshold similarity, and then comparing is performed for the additional motion model. For example, creating includes generating a temporal sequence of three-dimensional meshes and creating the additional motion model from the temporal sequence of the three-dimensional meshes. As a further example, the temporal sequence is generated from the contours, and creating includes generating multiple motion models by manifold learning and clustering.

In yet another embodiment, deforming and comparing are part of a minimization to identify a best fitting motion model from the first and at least one additional motion models. For example, the first and the at least one additional motion models are labeled with diagnoses, respectively, and displaying the information includes displaying the diagnosis for the first and the at least one additional motion models with the threshold similarity.

According to one embodiment, displaying includes displaying the information as a quantification of change over time from the first or additional motion model.

In a second aspect, a method is provided for shape determination of cardiac anatomy with a medical imager. The medical imager images a heart of a patient. The imaging generates images representing different planes of the heart at different times. A first motion model is selected to fit to the images. An improper fit is determined. An additional motion model is created in response to the improper fit. The additional motion model is fit to the images. A proper fit is determined. The shape based on the additional motion model and the images is displayed.

In one embodiment, creating includes generating a temporal sequence of three-dimensional meshes and creating the additional motion model from the temporal sequence of the three-dimensional meshes. For example, the temporal sequence is generated from contours extracted from the images, and creating includes generating multiple motion models by manifold learning and clustering.

In a third aspect, a method is provided for shape determination of cardiac anatomy with a medical imager. The medical imager images a heart of a patient. The imaging generates images representing short axis planes and long axis planes of the heart at different times. A chamber of the heart is contoured in the images for each of the different times. The contouring provides contours of the chamber in the short axis and long axis planes at each of the different times. The contours of the different planes are aligned for each of the different times. The aligning includes translating contours for the long axis planes relative to the contours of the short axis planes separately for each of the different times and finding a rotation of the contours for the long axis planes relative to the contours of the short axis planes based on fit across the different times. A motion model is fit to the contours as aligned over the different times. The motion model as fit provides the shape of the chamber. The shape is displayed.

According to one embodiment, aligning the contours includes aligning based on orientation and position information from the imaging and modifying by a rigid transform using the translation and rotation. The modification is based on a minimization of error relative to intersections of the contours from the long axis planes relative to the contours of the short axis planes.

In another embodiment, fitting includes testing different motion models and selecting the motion model based on the testing. The different motion models are labeled with different diagnoses. Displaying further includes displaying the diagnosis from the selected motion model.

These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Robust shape analysis of cardiac anatomy from 2D medical images is provided. Automatic segmentation, shape-based slice alignment, and learned motion models are leveraged to produce a sequence of 3D shapes from a set of 2D images. The motion mode information (fit model) together with estimated 3D shape may be displayed to assist in diagnosis. This robust 3D+t analysis of cardiac chamber shape systematically addresses various sources of error, such as image plane misalignment, motion variation, and poor image quality. In addition to providing a temporal sequence of 3D shapes optimally aligned and consistent with the available 2D images, this system also provides the estimated motion model best describing the heart chamber motion. This may be used as additional feature for subject classification and for risk stratification in patient populations.

Figure 1:
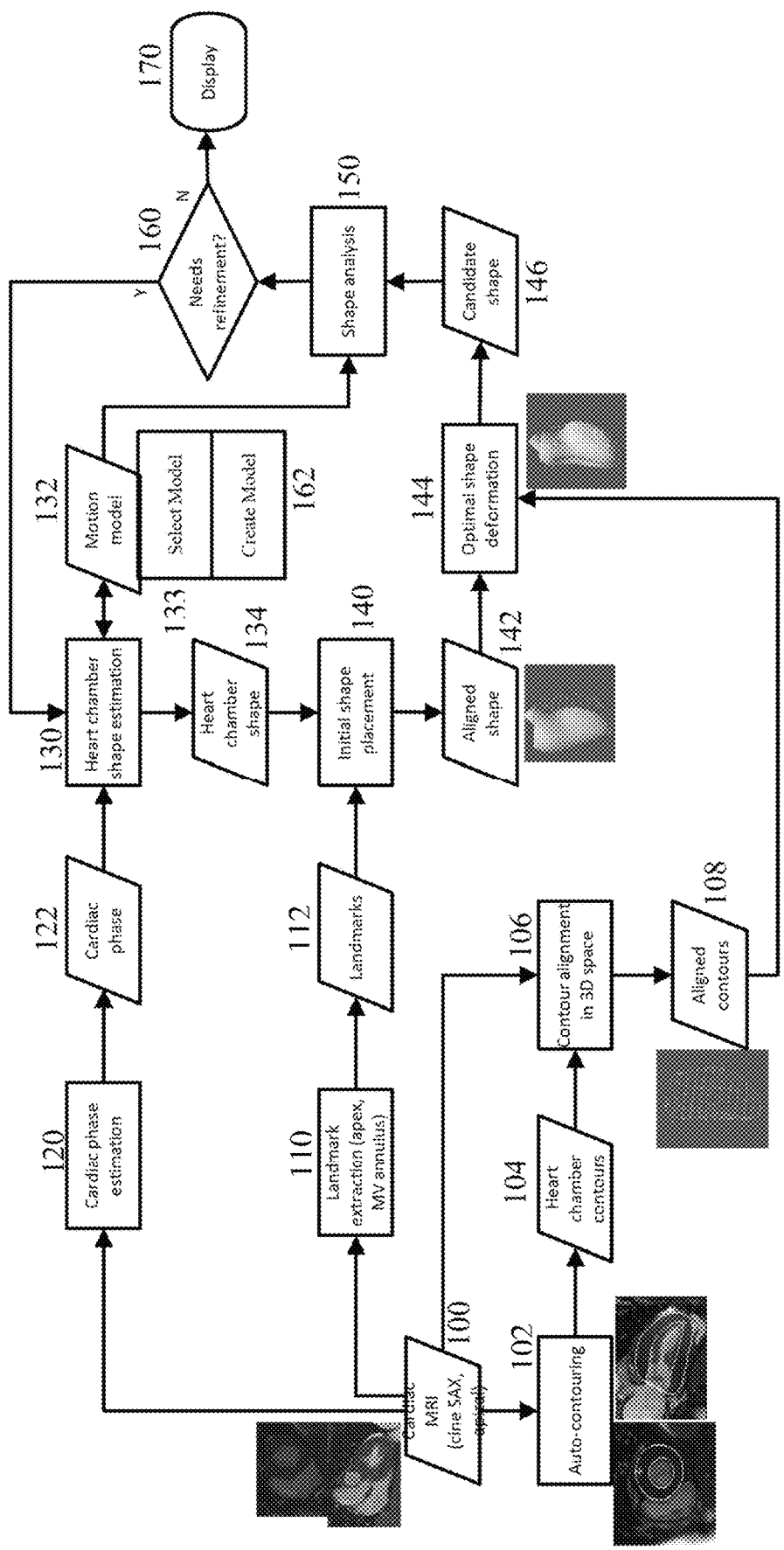
FIG. 1 is a flow chart diagram of one embodiment of a method for shape determination of cardiac anatomy with a medical imager.

FIG. 1 is a flow chart diagram of one embodiment of a method for shape determination of cardiac anatomy with a medical imager. A shape analysis system is provided for cardiac shapes, such as a heart chamber or other heart structure. The 3D shape over time, such as over a heartbeat, is determined from 2D images. By contouring, aligning contours, and selection of motion models for fitting, the 3D shape is determined accurately despite sources of error in the imaging. The aligning of contours may be improved by aligning in translation independently for different phases and by rotation across phases. The selection and fitting of models may be improved by creating a motion model on demand where the library of models does not provide a matching model or where a library is not used.

The method is performed in the order shown. Some acts may be performed in parallel or sequentially. Other orders may be used. For example, acts 102, 110, and 120 are performed in any order, in sequence, simultaneously, or interleaved.

Additional, different, or fewer acts may be provided. For example, acts 120, 110, or 140 are not performed, such as where ECG or timing is used to determine different times of imaging or initial shape placement is based on deformation in act 144 without landmark alignment. One of acts 106 or 162 may be provided without the other.

The method is performed by a medical diagnostic scanner, a workstation, a server, or a computer as the medical imager. The medical imager includes a scanner or memory for acquiring imaging data and one or more image processors for shape analysis. Remote, such as cloud based, or local processing may be used. For example, a scanner and/or memory are used to acquire or access images for a patient. A processor, such as an image processor of the scanner or a separate computer, performs shape analysis. The image processor uses a display screen or printer for display of the 3D shape and/or information derived therefrom. A physician may use the output information to assist in making a diagnosis and/or treatment decision for the patient. The information may result in better treatment and/or diagnosis for the patient.

In act 100, the medical imager images a heart of a patient. One or more medical diagnostic imaging systems image a patient. The imaging provides image data representing an internal cardiac region of the patient.

Computed tomography (CT) imaging, magnetic resonance imaging (MRI), x-ray angiography, fluoroscopy, optical, ultrasound, optical coherence tomography, and/or intravascular imaging and corresponding scanners may be used. For example, the heart of the patient is visualized using cardiac MRI. Contrast-enhanced (CE)-MRI may be used.

Figure 2A:
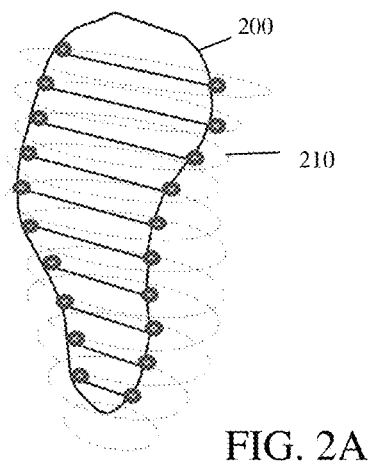
FIGS. 2A and 2B illustrate example intersections between contours for alignment refinement.
Figure 2B:
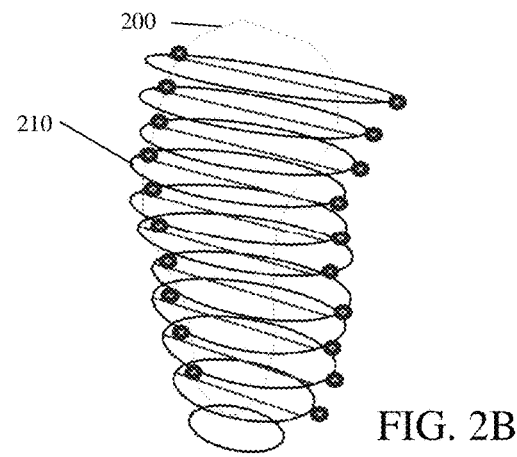

The volume of the cardiac region of the patient is imaged sparsely, such as 2D imaging of the patient. The imaging generates images representing different planes of the heart at different times. Each plane is scanned at each of the different times relative to the heart cycle (e.g., each of different cardiac phases even if during different heartbeats). Some or all of the planes may be parallel or substantially parallel (e.g., +/−10% angle). One or more of the planes may not be parallel (e.g., +/−11% or more angle, such as substantially orthogonal or perpendicular). For example, cardiac MRI images may include six or more (e.g., 10-16) short axis views substantially parallel with each other and two or more (e.g., 3-4) long axis views substantially perpendicular along at least one dimension to the short axis views. FIGS. 2A and 2B show an example with eleven short axis views corresponding to eleven short axis contours 210 and one long axis view corresponding to the one long axis contour 200. Other long axis views may be substantially parallel to each other and/or may be rotated relative to each other, such as about a vertical axis of the figures or long axis of the heart chamber.

Any number of images per heart cycle may be acquired. For example, each imaging plane is imaged four or more times (e.g., 10-20 times) per heart cycle. In one embodiment, the set of images includes a stack of short-axis views spanning the heart from base to apex and multiple long axis slices including for instance apical 2-, 3- and 4-chamber views. Each view is imaged as a temporal sequence of 2D images.

In act 102, the image processor contours a structure of the heart in the images of the different planes at the different times. Any structure or structures may be contoured, such as a chamber of the heart (e.g., left ventricle).

The contouring provides contours 104 of the structure in the different planes at the different times. Each contour 104 is a border or boundary of the heart structure. The contour 104 may be open or closed. A sequence of contours 104 of the structure is provided over the different times for each of the different planes.

The images are processed by a contouring algorithm to produce the temporal sequence of contours 104 for each view. Each contour 104 for a given time may be determined independently. Alternatively, the contouring determines the contours for a given plane over time (i.e., through the sequence) based, at least in part, on the contours of other times. The contours 104 for a given view or plane are determined independently of other planes. Alternatively, the contouring determines the contours 104 for a given plane based, at least in part, on contours 104 of other planes.

Any contouring algorithm capable of producing such sequence of contours 104 can be utilized. For instance, random walker, pattern matching, thresholding, shape fitting, or other processes are used to segment the border of the structure. As another example, algorithms based on convolutional neural networks or other machine-learned models for image segmentation are used. Any machine-learned model resulting from machine training may be used. For example, a support vector machine, clustering, or other generator is trained to generating the contour 104 given an input image. In one embodiment, a neural network, such as a U-Net, image-to-image, encoder-decoder, or generator, is trained to generate the contour 104. The neural network may be a fully connected network and/or a convolutional neural network (CNN).

Figure 3A:
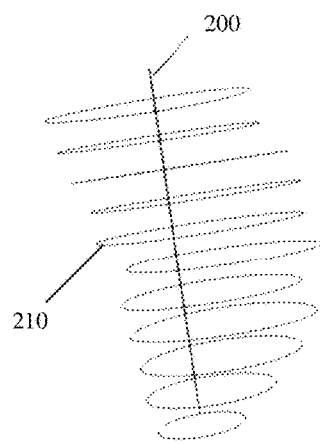
FIG. 3A-C illustrate example translations of a long axis contour relative to short axis contours.
Figure 3B:
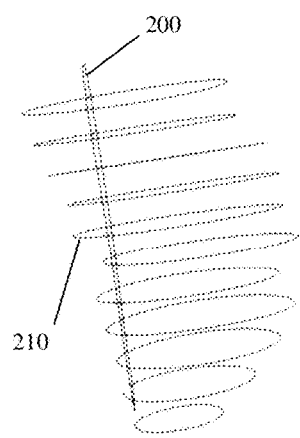
Figure 3C:
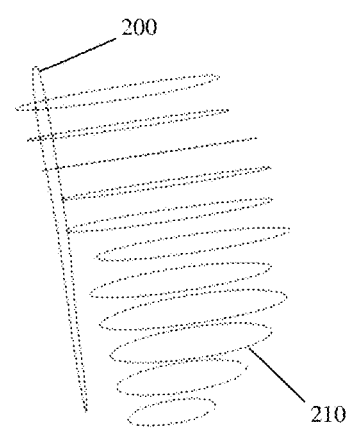

FIG. 3C shows an example of chamber contours 200, 210 generated by the image processor using segmentation. A short axis contour 210 of the chamber is provided for each short axis view or plane. A long axis contour 200 is provided for each long axis view or plane. In this example, the long axis contour 200 is misaligned in 3D space relative to the short axis contours 210 since the long axis contour 200 does not intersect valid chamber contours 210 in multiple short axis planes. The misalignment is corrected through alignment in act 106, initial placement in act 140, and/or deformation in act 144.

In act 106, the image processor aligns the contours of the different planes for each of the times. Any misalignment is corrected. This alignment of contours corresponds to alignment of the imaging planes. Where the contouring is independent for each view or plane and/or time, the image processor corrects the misalignment.

In one approach, the alignment is based on orientation and position information from the imaging. The position of the patient relative to the scanner and/or plane position relative to the scanner are used to align. The chamber contours produced in the auto-contouring are aligned in 3D space using the orientation and position information associated to the original images at the time of acquisition by the MRI scanner.

After this alignment, the contours 200, 210 may have inconsistent position or orientation. For example, one or more contours 210 from short axis images do not intersect one or more planes containing contours 200 coming from longitudinal axis images as shown in FIG. 3C. This can be due to multiple reasons including patient motion, respiratory motion artifacts, or incorrect slice planning.

In an additional or alternative approach, the image processor modifies the initial alignment. The alignment based on orientation and position from the imaging may be modified. For example, the modification adjusts each long-axis contour 200 relative to the short axis contours 210. A rigid transform of the contour 200 from the long axis plane relative to the contours 210 of the short axis planes is performed. The transform may be in translation only, rotation only, or both rotation and translation. Scaling may or may not be used. The translation and/or rotation may be along any number of degrees of freedom, such as translation along three dimensions and rotation about one or two dimensions.

A fitting to maximize the intersections of the long axis contour 200 with the short axis contours 210 is performed. In one embodiment, the rigid transform is based on a minimization of error for intersections of the contour 200 from the long axis plane relative to the contours 210 of the short axis planes. The image processor modifies the slice alignment based on intersections. Another criterion or criteria may be used, such as difference from a 3D contour model where both short axis 210 and long axis 200 contours are translated and/or rotated in the optimization.

In one embodiment, the short axis images are selected as the reference, and each long axis image is aligned to the short axis images. Each long axis image or corresponding contour 200 is moved to test different positions, as depicted in FIGS. 3A-C. Only positions of the long axis plane and contour 200 such that the long axis plane crosses the most short axis planes and contours 210 are kept. For each of the considered positions of the long axis plane, two sets of points are computed, as shown in FIGS. 2A and 2B. The sets of points are the initial points and the wanted points. The initial points are derived from the trace of the long axis contour 200 on the short axis planes. In FIG. 2A, the bold lines represent the projection of the long axis contour 200 on the short axis planes, and the initial points are represented as dots. The wanted points are derived from the traces of the short axis contours 210 on the long axis plane. In FIG. 2B, the bold lines represent the projection of the short axis contours 210 on the long axis plane, and the wanted points are represented as dots at the desired intersections. A matrix R* and a vector t* are computed for a rigid transformation to minimize the error E:

$$R^*, t^* = \underset{R,t}{\operatorname{argmin}} \sum_{i=1}^{n} \|Rp_i + t - q_i\|^2 \text{ and } E = \sum_{i=1}^{n} \|R^* p_i + t^* - q_i\|^2$$

with $P_n$ initial points, and $Q_n$ wanted points. The position and transformation that minimize the error E are kept as the alignment.

In an additional or alternative embodiment, the image processor aligns the contour 200 from the long axis view relative to the contours 210 of the short axis views in translation for each of the different times. The translation in any number of degrees of freedom is found to maximize the intersections and/or minimize an error separately and/or independently for each time. The result is a sequence of translations that may or may not be the same. The average, median, or other combination across time for translation is found.

Figure 4:
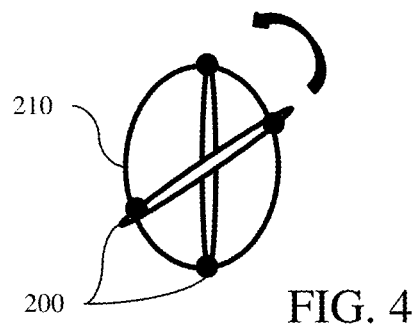
FIG. 4 illustrates an example rotation of a long axis contour relative to a short axis contour.

The rotation is handled separately from the translation. The rotation is found as a single fit over time of the translation (i.e., from combinations of the translations at different times) or other translations from different times prior to combination. FIG. 4 shows an example rotation of the long axis contour 200 relative to the short axis contour 210 to maximize the fit by placing the intersections at the edge. The rotation is found as one rotation for the sequence or across all the times. The rotation is a single fit for all the different times using the translation for each of the different times. A rotation of the contours 200 for the long axis planes relative to the contours 210 of the short axis planes is found based on fit across the different times.

In alternative embodiments, the translation and rotation are solved together for each time and/or across times, the rotation is solved first and followed by the translation for each time or across times, and/or the rotation is solved for each time and the translation across all times.

The alignment results in aligned contours 108. The aligned contours 108 provide a sparse representation of the 3D heart structure.

In act 110, the image processor identifies anatomical landmarks 112 of the heart from the images. The anatomical landmarks 112 are detected or found to provide an initial alignment of the motion model 132 with the contours 108.

The landmarks 112 may be for the heart volume so may be on or near the contours 200, 210 and/or may be spaced from the contours 200, 210 (108). Any number of landmarks 112 may be identified. Any of various landmarks 112 of the heart may be used. In one embodiment, a left ventricle apex, mitral valve annulus points, right ventricle insertion points, tricuspid valve points, and/or pulmonary veins ostia are detected. Additional, different, or fewer landmarks 112 may be used.

The landmarks 112 are found from the images. The landmarks 112 are found from the images for each of the different times, providing position of landmarks relative to contours 108 for each time.

Any landmark detection may be used, such as pattern matching. In one approach, segmentation is used, such as with a CNN or other machine-learned model to detect the landmarks 112. In another approach, an image search uses deep reinforcement learning to detect the landmarks 112.

In act 120, the image processor determines a cardiac phase for each of the different times from the images. Each of the different times corresponds to a different part of the cardiac cycle.

In one approach, the timing between imaging is used without a more specific phase determination. Each time represents a different part of the cycle without identification of the specific part.

In another approach, the image processor determines one of the different times as end diastole and another of the different times as end systole. Other times are identified relative to these two times. For example, the temporal sequence of images is processed for the estimation of the cardiac phase in each image frame. Cardiac phase estimation includes the identification of an end diastolic frame (ED), an end systolic (ES) frame, and associating each frame in the image sequence with a value in the range [0, 1], representing the percentage of the heart cycle (e.g., ED frame being assigned value 0, ES frame being assigned a value strictly comprised between 0 and 1, and the value 1 representing the beginning of the next heart cycle). The different times are then grouped relative to the heart cycle. Alternatively, images represent specific points in addition to or other than ED or ES may be identified.

The cardiac phase may be determined from ECG acquired when the images were acquired. The acquisition provides the phase. Alternatively, the cardiac phase for each time is estimated from the sequence of images. Images over time for one view or multiple views are processed to identify the cardiac cycle, such as an average intensity mapped over time showing the cycle. In one example, the area in the contours 200 and/or 210 is used. In other examples, a machine-learned model (e.g., CNN) receives the images as input and outputs a classification for each time as the cardiac phase 122.

In acts 130, 140, and 144, the image processor fits a motion model 132 to the contours 108 as aligned over the different times or phases 122. The motion model 132 as fit provides the 3D shape of the heart structure (e.g., chamber). The motion model 132 is a 3D representation of the structure over time, such as a 3D mesh (e.g., triangular mesh) over time showing motion as a spatial representation over time. Other motion models 132 may be used, such as vectors or motion parameterization relating shape over time.

In one approach, the image processor initializes a shape in act 130, the shape is aligned in act 140, and the shape is refined by deformation in act 144. Other combinations of acts may be used, such as using initialization in act 130 and deformation in act 144 without an initial alignment in act 140 (e.g., alignment handled as part of the deformation process rather than separately).

In act 130, the expected shape is generated based on a motion model 132. The motion model 132 may be selected in act 133 from a library or collection of motion models 132. The heart chamber shape estimator of the image processor selects one of the multiple motion models 132 and uses the model 132 to produce a 3D shape corresponding to a cardiac phase 122 provided as an input. The selection may be based on expected diagnosis, characteristic of the patient, characteristic in the images, and/or shape of contours. The selection of the motion model 132 to use may be random in the first instance, and informed by the shape analysis 150 in subsequent instances, such as selecting based on differences between a previously selected model 132 and the fit shape 146. Alternatively, only one motion model 132 is provided. In another alternative, no motion model 132 is provided, and the contours 108 are used to create a motion model.

Once the motion model 132 is selected in act 133, the motion model 132 is used to generate a shape 134. The image processor estimates an expected shape 134 in 3D at a given phase 122 or for each phase 122. The motion model 132 indicates the shape 134 over time or for each of the phases 122 for which images were acquired in act 100.

In act 140, the image processor aligns the shapes 134 estimated from the motion model 132 with the anatomical landmarks 112 for the different times or phases 122. The heart chamber shape 134 produced by the estimator is aligned with the current contours 108 based on the detected landmarks 112. The alignment is a rigid transform with or without scaling. Non-rigid transformation may be used.

The shape alignment may be based on thin plate spline interpolation, using a known correspondence between certain anatomical landmarks 112 and specific points in the triangular mesh of the shape 134. Other translation, rotation, and/or scaling may be used. This alignment deforms and/or positions, orients, and scales the estimated chamber shape 134 in a manner consistent with the known location of a subset of its points (i.e., the landmarks 112). The result is placement of the shapes 134 to match with the structure represented by the contours 108 over the different phases 122. The aligned shapes 142 for the different phases 122 are provided.

In act 144, the image processor deforms the aligned shape 142, refining the alignment, using the contours 108. For each time or phase 122, the image processor deforms an aligned or placed shape 142 from the motion model 132 to the contours 108 as aligned with each other in act 106. The deformation is based, in part, on the anatomical landmarks 112 through the initialization or initial placement in act 140. Non-rigid deformation is used.

The shape deformation in act 144 further deforms the aligned chamber shape 142 to maximize the similarity with the aligned contours 108 provided as an input. The mesh points are deformed so that the distance between each contour point and the triangular surface is minimized. Any fitting may be used, such as an optimization or minimization of differences. Mesh points without corresponding contour points may be translated to minimize difference from the surrounding mesh points that have a corresponding contour point. The mesh is fit to the contours 108, providing a 3D representation or candidate shape 146 of the heart structure based on the shape 142 from the model 132 and the aligned contours 108.

In act 150, the image processor determines whether the fit (e.g., initial placement in act 140 and deformation of act 144) is proper or acceptable. A shape analysis is performed on the candidate shape 146 to determine whether the motion model 132 is the correct motion model 132 for the patient.

The image processor compares the deformed or candidate shape 146 to the original shape 134 of the motion model 132 in act 150. The deformed shape 146 of the mesh fit to the aligned contours 108 represents the 3D shape 146 of the structure of the patient. After deformation, the shape 146 is analyzed to determine its consistency with the motion model 132 selected initially. The difference between meshes is computed as point-to-point distance or point-to-surface distance. Other differences between meshes may be used. The difference indicates the amount of similarity between the mesh as fit to the patient structure and the mesh prior to fitting.

When the comparison in the shape analysis shows a threshold similarity, this candidate shape 146 is output as the 3D shape for the phase or phases 122. The candidate shape 146 is sufficiently like the shape 134 of the model 132. The comparison is done for each of the phases 122 to find the model 132 matching the motion modes of the structure of the patient.

When the difference between the deformed mesh and the estimated heart chamber shape 134 exceeds a pre-determined threshold, then the shape 146 needs refinement and a new heart chamber shape estimation procedure (act 130) is initiated in act 160. A different motion model is selected in act 133 for estimation in act 130. The estimation of act 130, placement of act 144, deforming of act 144, and comparing of act 150 are performed for the new model. These acts may be repeated for other models 132 when the comparison of act 150 does not show the threshold similarity. The acts are repeated until the comparison shows the threshold similarity with one of the additional motion models 132.

The acts for finding a properly fitting model are part of a minimization to identify a best fitting motion model 132 from the library or other set of motion models 132. The differences between resulting candidate shapes 146 for the set of motion models 132 are analyzed to find the one with the minimum difference. The various motion models 132 are fit to the images to find or determine a sufficiently similar model 132 (proper fit of act 160) to the structure of the patient.

In one embodiment, the heart chamber shape estimation act 130 is used in the identification of the best motion model index. Each shape 134 is represented by a mesh with a defined number of points. A motion model 132 is defined as a sequence of a defined number of meshes representing one heart beat. The meshes of a motion model 132 are defined in a normalized reference system and are mapped to physical space via TPS transformation, for instance. Assuming that multiple motion models 132 are available, the index I of the best motion model 132 is defined by the following relationship:

$$I = \operatorname*{argmin}_{i}\left(\sum_{t=0}^{27} E_{tps}(X_t, M_{i,t}, T)\right)$$

with $X_t$ a mesh in physical space at time=t, $M_{i,t}$ the $i^{th}$ motion model 132 at time=t, T the current TPS transformation and $E_{tps}(X,M,T)=\Sigma_k^{cn}\|T(X_k)-M_k\|^2+\delta f(T)$, with k being the index of control points and cn the number of the control points. Control points are selected points from both the mesh in physical space and from the motion model 134. The control points y are a smaller number than the total number of points in the meshes. δ is a scalar acting as a weight, and f indicates the smoothness of the transformation. I stands for the index of the best computed motion model 132. The best or sufficient computed motion model 132 identified through the minimization is transformed to physical space by TPS transformation, obtaining the estimated heart chamber shape (candidate shape 146).

The library of motion models 132 may be created in various ways, such as by curating various representative cases. In one approach, machine learning or application of a machine-learned model is used to generate motion models 132 from 3D+t meshes or other sources of information (e.g., contours 108). For example, the motion models 132 are learned based on expert annotations of training data, as described in L. Yang, B. Georgescu, Y. Zheng, Y. Wang, P. Meer, D. Comaniciu: Prediction-based Collaborative Trackers: A Robust and Accurate Approach toward 3D Medical Object Tracking, IEEE Trans. Medical Imaging, 30(11): 1921-1932, 2011 (Reference 1).

The motion models 132 may include various information, such as quantities and/or labels related to the motion mode represented by the model 132. By finding the best or sufficiently fitting model, information about the motion mode of the patient is identified. For example, the motion models 132 represent different diagnoses. By finding the sufficiently fitting model 132, the diagnosis for the patient is given by the diagnosis from the selected model 132. Ejection fraction and/or other quantities corresponding to flow may be provided by the model 132. Alternatively, the model 132 as fit to create the candidate shape 146 is used to calculate the quantity.

In act 162, the image processor creates one or more additional motion models 132 in response to the improper fit as determined in act 160. The additional motion model 132 is created on demand when the comparison of act 150 to the previously used motion model 132 does not show the threshold similarity. The process is then repeated for the created motion model 132 to test whether a sufficient or proper fit is provided.

To create a motion model 132 on demand, the image processor generates a temporal sequence of three-dimensional meshes. The additional motion model 132 is created by alteration of the temporal sequence of the three-dimensional meshes, such as altering the 3D+t meshes as created as the motion model 132. In one implementation, the contours 108 as aligned are extrapolated into a 3D mesh for each phase 132. Multiple motion models 132 may be created by adding variation to the 3D mesh, such as using modeling of different common or possible variations in the structure.

In another implementation, the temporal sequence is generated from the contours 108. The different motion models 132 are then created by manifold learning and clustering. The learning of the motion models 132 can be based on estimated 3D shapes obtained with the shape analysis system (e.g., outputs of the candidate shapes 146). In this case, the shape analysis system is applied to a large set of images constituting a training set. The motion model 132 can be replaced by a module producing a single mean mesh for any given cardiac phase. Application of the shape analysis system above with this modification yields a temporal sequence of 3D meshes for each set of images.

Further motion models and/or selection of models 132 to include or create may be determined by application of the analysis performed in Reference 1. The approach of reference 1 may be used to create additional motion models 132 from a given sequence of meshes. The motion models 132 can be updated (created on demand) by applying the shape analysis system iteratively as follows: first, run the shape analysis system using a single mean mesh as the motion model 132, then obtain a first set of additional motion models 132 by application of the process of Reference 1, then run the shape analysis system with the first set of motion models 132 to provide further mesh sequences (candidates 146), then obtain an updated set of motion models by application of the process of Reference 1, and so on. If the number of obtained motion models 132 is unchanged over an iteration of application of the process of Reference 1, the creation terminates. Otherwise, another iteration of running the shape analysis system with the updated set of motion models 132 is performed. This repetition continues until the number of models is unchanged after an iteration. A limit on the number of models 132 created may be used.

Reference 1 teaches prediction-based collaborative trackers (PCT). A forward prediction generates the motion prior using motion manifold learning. Collaborative trackers achieve both temporal consistency and failure recovery. The PCT applies a motion prior learned on a low dimensional manifold to constrain the collaborative trackers including a detection tracker and a template tracker. Robust information fusion is applied to generate a joint posterior probability. Motion prediction is performed using registration guided one step forward prediction. The motion modes are learned by motion alignment using 3D generalized Procrustes analysis, motion manifold learning, and hierarchal K-means clustering. A phase detector may be learned using principal components analysis shape space based on marginal space learning. Boundary classifiers may be learned to initialize the trackers. The tracking uses the one-step forward prediction using the learned motion modes. The collaborative trackers use the learned motion prior from the one-step forward prediction on the motion manifold to search for the boundary. Fusion of the collaborative tracking is obtained by prior distributions. The whole procedure is performed periodically. Other approaches may be used, such as by tracking by detection and 3D optical flow.

In an alternative implementation, the motion model 132 is created from simulated cardiac chamber motion obtained, for example, from a computational model of heart biomechanics. By varying parameters of the computational model, various motion models 132 may be created for the library and/or on demand. Simulated motion models 132 may include irregular beat-to-beat motion due, e.g., to arrhythmias. This allows the system to identify such abnormal motions and therefore enables robust shape analysis also in the presence of irregular rhythm.

In act 170, the image processor, using a display, displays the candidate shape 146 indicated as sufficient by the comparison in act 150. An image showing a rendering of the 3D shape 146 or cross sections (e.g., multiplanar reconstruction) is displayed. The images acquired in act 100 may be displayed with a graphic overlay of the candidate shape 146. A video showing the shape 146 over time (e.g., over the phases 122) may be displayed.

Other information may additionally or alternatively be displayed. For example, information based on the candidate shape 146 is determined. A quantity, such as ejection fraction, volume at end systole, volume at end diastole, volume flow, and/or another quantity, is calculated from the shape, such as using fluid dynamics. A quantification of change in shape over time may be calculated. A quantity or quanitites may be displayed. As another example, a diagnosis and/or other information linked to the motion model 132 found to sufficiently fit in act 160 is displayed. In yet another example, a prediction of disease risk based on the shape or on the motion model may be displayed.

Figure 5:
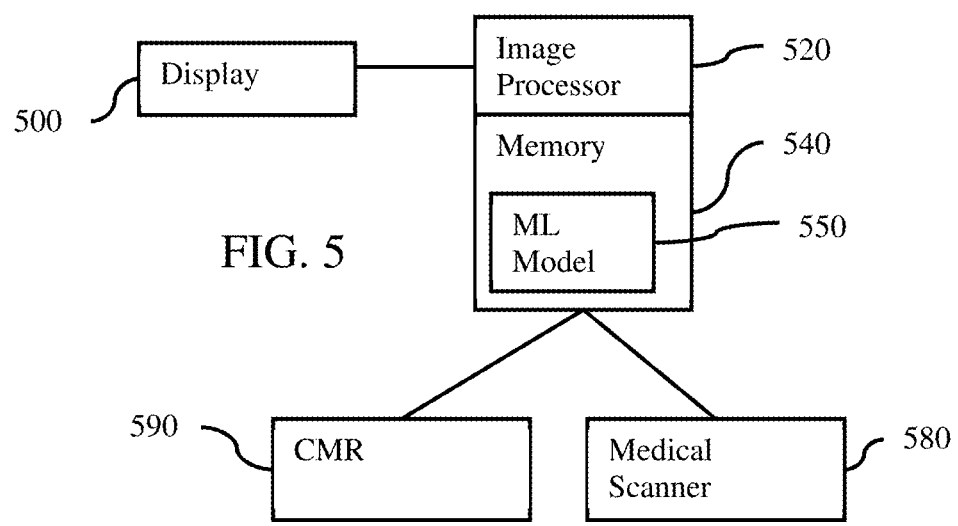
FIG. 5 is a block diagram of one embodiment of a system for shape determination of cardiac anatomy with a medical imager.

FIG. 5 shows one embodiment of a medical system or imager for shape determination of cardiac anatomy with a medical imager. The system fits a motion model to imaging for a patient, providing a 3D shape from 2D imaging. The system or imager performs the method of FIG. 1 or another method.

The medical system includes the display 500, memory 540, and image processor 520. A computerized medical records database 590 and/or medical scanner 580 may be included in the medical imager or system. The display 500, image processor 520, and memory 540 may be part of the medical scanner 580, a computer, server, workstation, or other system for image processing medical images from a scan of a patient. A workstation or computer without the medical scanner 580 and/or computerized medical record database 590 may be used as the medical system or imager.

Additional, different, or fewer components may be provided. For example, a computer network is included for remote image processing or data storage based on locally captured scan and/or other imaging data. As another example, a user input device (e.g., keyboard, buttons, sliders, dials, trackball, mouse, or other device) is provided for user input.

The medical scanner 580 is a computed tomography, magnetic resonance, ultrasound, fluoroscopy, x-ray, optical coherence tomography, intracardiac imaging, or another mode of scanner. For example, the medical scanner 580 is a computed tomography system having an x-ray source and detector connected to a moveable gantry on opposite sides of a patient bed. As another example, the medical scanner 580 is a cardiac MRI scanner using a main magnet, gradient coils, local coils, and/or body coil.

The medical scanner 580 is configured by settings to scan a patient. The medical scanner 580 is setup to perform a scan for the given clinical problem, such as a cardiac scan. The scan samples in the patient along 2D planes over at least one heartbeat. The scan results in scan or image data that may be processed to generate images of the interior of the patient on the display 500.

The image processor 520 is a control processor, general processor, digital signal processor, three-dimensional data processor, graphics processing unit, application specific integrated circuit, field programmable gate array, artificial intelligence processor or accelerator, digital circuit, analog circuit, combinations thereof, or other now known or later developed device for processing medical image data. The image processor 520 is a single device, a plurality of devices, or a network. For more than one device, parallel or sequential division of processing may be used. Different devices making up the image processor 520 may perform different functions. In one embodiment, the image processor 520 is a control processor or other processor of a medical diagnostic imaging system, such as the medical scanner 580. The image processor 520 operates pursuant to stored instructions, hardware, and/or firmware to perform various acts described herein.

In one embodiment, the image processor 520 is configured to contour, align image planes and/or contours, detect landmarks, estimate cardiac phase, select a model, create a model, estimate shape, place shape relative to landmarks, deform the shape based on the contours, analyze the shape as fit, and decide whether to repeat with a different model. Any of the acts of FIG. 1 may be performed by the image processor 520. One or more acts may use a machine-learned model 550. The image processor 520 determines a shape over time, such as a 3D mesh fit to contours extracted from the 2D imaging over a heartbeat.

The image processor 520 may be configured to align contours using translation by phase and rotation across the phases (i.e., one rotation found or solved for all the phases verses translation being found or solved for each phase). Other alignment sequences may be used. The image processor 520 may be configured to create one or more motion models on demand or for shape determination for a given patient. Alternatively, available motion models are used without creating any for a given patient.

The image processor 520 is configured to generate an image. The image shows the determined shape, a quantity derived from the determined shape, a diagnosis from the selected motion model, other information from the motion model or determined shape, and/or images from the imaging (e.g., sequence of 2D images of different views of the patient).

The display 500 is a CRT, LCD, projector, plasma, printer, tablet, smart phone, or other now known or later developed display device for displaying the output, such as an image with the information from the model and the MRI images.

The training data, machine-learned models 550, image data, non-image data, detected landmarks, contours, motion models, diagnosis, cardiac phase, alignment, deformation, and/or other information are stored in a non-transitory computer readable memory, such as the memory 540. The memory 540 is an external storage device, RAM, ROM, database, and/or a local memory (e.g., solid state drive or hard drive). The same or different non-transitory computer readable media may be used for the instructions and other data. The memory 540 may be implemented using a database management system (DBMS) and residing on a memory, such as a hard disk, RAM, or removable media. Alternatively, the memory 540 is internal to the processor 520 (e.g., cache).

The instructions for implementing, by execution by the processor 520, the acts, the methods, and/or the techniques discussed herein are provided on non-transitory computer-readable storage media or memories, such as a cache, buffer, RAM, removable media, hard drive, or other computer readable storage media (e.g., the memory 540). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the way the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for shape determination of cardiac anatomy with a medical imager, the method comprising:
    imaging, by the medical imager, a heart of a patient, the imaging generating images representing different planes of the heart at different times;
    contouring a structure of the heart in the images of the different planes at the different times, the contouring providing contours of the structure in the different planes at the different times;
    identifying anatomical landmarks of the heart from the images;
    determining a cardiac phase for each of the different times from the images;
    aligning the contours of the different planes for each of the times corresponding to the cardiac phases;
    deforming a shape from a first motion model to the contours as aligned with each other, the deforming based in part on the anatomical landmarks;
    comparing the deformed shape from the first motion model to the shape from the motion model, wherein the deformed shape is the shape of the structure of the patient when the comparison shows a threshold similarity and wherein the deforming and comparing are performed for at least one additional motion model when the comparison does not show the threshold similarity until the comparison shows the threshold similarity with one of the at least one additional motion models; and
    displaying information from the first or additional motion model where the comparison shows the threshold similarity and the shape.

2. The method of claim 1 wherein imaging comprises cardiac magnetic resonance imaging with six or more short axis views and two or more long axis views as the different planes for each of at least four different times, the different times being over a heart cycle, and wherein at least a first one of the different planes is not parallel to second and third ones of the different planes.

3. The method of claim 1 wherein contouring comprises generating a sequence of contours of the structure over the different times for each of the different planes, the structure comprising a heart chamber.

4. The method of claim 1 wherein identifying comprises identifying a left ventricle apex, mitral valve annulus points, right ventricle insertion points, tricuspid valve points, and pulmonary veins ostia in the images for each of the different times.

5. The method of claim 1 wherein determining the cardiac phase comprises determining one of the different times as end diastole and another of the different times as end systole.

6. The method of claim 1 wherein aligning the contours comprises aligning based on orientation and position information from the imaging and modifying by a rigid transform of the contour from the first plane relative to the contours of the second and third planes based on a minimization of error relative to intersections of the contour from the first plane relative to the contours of the second and third planes.

7. The method of claim 1 wherein aligning comprises aligning the contour from the first plane relative to the contours of the second and third planes in translation for each of the different times and in rotation as a single fit for all the different times using the translation for each of the different times.

8. The method of claim 1 wherein deforming comprises selecting the first motion model from a library of motion models, aligning meshes of the first motion model with the anatomical landmarks for the different times, and refining the alignment using the contours.

9. The method of claim 1 further comprising creating the additional motion model on demand when the comparison to the first motion model does not show the threshold similarity, and then comparing for the additional motion model.

10. The method of claim 9 wherein creating comprises generating a temporal sequence of three-dimensional meshes and creating the additional motion model from the temporal sequence of the three-dimensional meshes.

11. The method of claim 10 wherein the temporal sequence is generated from the contours, and wherein creating comprises generating multiple motion models by manifold learning and clustering.

12. The method of claim 1 wherein deforming and comparing are part of a minimization to identify a best fitting motion model from the first and at least one additional motion models.

13. The method of claim 12 wherein the first and the at least one additional motion models are labeled with diagnoses, respectively, and wherein displaying the information comprises displaying the diagnosis for the first and the at least one additional motion models with the threshold similarity.

14. The method of claim 1 wherein displaying comprises displaying the information as a quantification of change over time and/or a disease risk from the first or additional motion model.

* * * * *